United States Patent [19]
Simmons

[11] Patent Number: 5,891,052
[45] Date of Patent: Apr. 6, 1999

[54] DIAGNOSTIC SYRINGE ACTUATOR DEVICE

[76] Inventor: Paul L. Simmons, 8825 Laurel Dr., Pinellas Park, Fla. 33782

[21] Appl. No.: 882,570

[22] Filed: Jun. 25, 1997

Related U.S. Application Data

[60] Provisional application No. 60/020,624, Jun. 26, 1996.
[51] Int. Cl.[6] ............................. A61B 5/00; B65D 81/00
[52] U.S. Cl. ........................... 600/573; 600/578; 604/38; 604/181; 604/187; 604/220
[58] Field of Search ..................................... 600/573, 576, 600/578, 579, 577, 580; 604/38, 187, 218, 221, 181, 208, 220, 228

[56] References Cited

U.S. PATENT DOCUMENTS

| | | | |
|---|---|---|---|
| 4,231,368 | 11/1980 | Becker | 604/157 |
| 5,183,465 | 2/1993 | Xanthakos et al. | 604/108 |
| 5,241,969 | 9/1993 | Carson et al. | 600/565 |
| 5,535,746 | 7/1996 | Hoover et al. | 600/432 |
| 5,666,966 | 9/1997 | Horie et al. | 600/573 |
| 5,709,667 | 1/1998 | Carilli | 604/187 |

Primary Examiner—Richard J. Apley
Assistant Examiner—Justine R. Yu
Attorney, Agent, or Firm—A. W. Fisher, III

[57] ABSTRACT

A diagnostic syringe actuator device for use in combination with a syringe in the removal of tissue, fluid and/or cells for the diagnosis of pathological processes wherein the syringe includes a hollow syringe body having a longitudinally movable syringe plunger at least partially disposed therein with a probe needle attached to the distal end portion comprising a hollow retractor tube having a longitudinally movable retractable piston disposed therein, a longitudinally movable syringe plunger sabot disposed within the hollow retractor tube, a sabot lock mechanism selectively movable between a locked and unlocked position disposed to engage the syringe plunger sabot when in the locked position to maintain the syringe plunger and the syringe plunger sabot in the advanced position and to disengage the syringe is plunger sabot when moved to the unlocked position such that the syringe plunger sabot and the syringe plunger move from the advanced position when the retractable piston has been at least partially retracted within the hollow retractor tube creating a vacuum therein whereby material is extracted from a patient through the probe needle and into the hollow syringe body.

12 Claims, 2 Drawing Sheets

DIAGNOSTIC SYRINGE ACTUATOR DEVICE

CROSS REFERENCE

This is a regular patent application claiming priority and converted from the provisional patent application filed Jun. 26, 1996 assigned application Ser. No. 60/020,624.

BACKGROUND OF THE INVENTION

1. Field of the Invention

A retractable piston syringe adapter for use in combination with a syringe in the removal of human tissue, fluid and/or cells for the diagnosis of pathological processes.

2. Prior Art

The pathological diagnostic technique of fine needle aspiration has become widely used.

An example of the technique which can be performed in a doctor's office, allows diagnosis of lesions, such as breast masses. In this technique a needle is inserted through the skin into the mass, organ, sack and a vacuum is applied to aspirate or withdraw cells or fluid from the target. The vacuum is created by withdrawing the syringe plunger. During the vacuum state, the user moves the needle up and down with one hand, causing cells, tissue and/or fluid to be cut free so that the vacuum will suck them into the barrel of the syringe. When an adequate sample is obtained, the vacuum is exhausted. The needle is withdrawn.

Needle aspiration usually involves a disposable syringe with an attached disposable needle. A syringe holder is presently used with the syringe, although the syringe may be used by hand without the holder. The syringe holder is a device made of a solid material such as metal, in which the disposable syringe and needle is inserted. The syringe holder allows the user to operate the syringe, including withdrawing its plunger with one hand, U.S. Pat. No. 2,198,666 describes a syringe having a body and plunger to take up and expel fluid including a resilient spring that operatively engages the plunger to urge the plunger outwardly of ii the body and interlocking means operatively connected to the plunger and the body to position the plunger relative to the body in at least one intermediate position. The interlocking means comprises an engageable finger and recess means adapted to selectively accommodate the finger having a shoulder positively preventing outward movement of the plunger by the spring and provide a free passage in the opposite direction whereby the plunger may be freely actuated to expel the contents of the syringe against the spring tension only and a second passage disposed axially of the syringe open ended in both axial directions for permitting movement of the plunger completely out of the body.

U.S. Pat. No. 5,241,969 shows a syringe holder for the diagnostic technique of fine needle aspiration used in the diagnosis of cancer and other pathological processes. A stabilizing ring with or without a detachable extended stabilizing ring is placed on the skin around the mass which is to be needled. The needle is guided into the mass accurately as the syringe is held firmly by a syringe body holder which slides on guide bars. A vacuum is created by pulling the syringe plunger back with a plunger holder and cells and tissue from the mass are sucked into the syringe as the needle is moved in an up-and-down direction by the hand holding a handlebar. The depth of needle penetration is controlled by limit screws. When the sample is obtained, the vacuum is released. The needle is removed from skin and the sample is removed from the syringe.

U.S. Pat. No. 4,850,973 teaches an injection device adapted to fit various syringe sizes. The injection device is spring loaded and provides a firing barrel which in the cocked position is offset slightly from the central bore of the device. When the device is fired, the firing barrel is aligned with the central bore and projects the needle portion of the syringe into the user. For obtaining blood samples, the syringe is replaced by a striker element which actuates a spring loaded puncture module which punctures the skin and is quickly withdrawn.

U.S. Pat. No. 5,141,496 describes a syringe guide with adjustment of the depth to which the needle penetrates comprising a body having one end provided with a sliding base which is adjustable in position by means of a screw and whose other end includes a sliding part fixed to the syringe and loaded by a spring which on relaxing causes the needle to be plunged into the skin to a predetermined depth.

U.S. Pat. No. 5,250,026 shows an implant injector for animals adjustable for implant insertion depth. The distance that the injector needle or cannula extends past the nose of the injector is adjustable. The insertion depth adjustment is accomplished by moving the nose of the injector relative to the tip of the cannula that extends past the nose. In addition to adjusting the insertion depth, the cannula or needle may also be rotated to a plurality of positions relative to the injector handle. A spring loaded plunger, when released by a release button, will push the implant out the end of the cannula as the operator withdraws the cannula from the animal. The release button is designed as a safety trigger to avoid premature activation of the plunger during insertion of the needle. Needles or cannulas of various diameters and lengths may be interchanged in the injector. The spring loaded plunger for expelling the implant may be removed allowing the operator to replace the plunger with a different diameter and length plunger to match different size cannulas.

U.S. Pat. No. 5,104,380 teaches a syringe comprising a dose metering device provided by a cap rotatable with respect to a pen body to a position related to the dose of medicament to be injected. The rotation compresses a coil spring which is prevented from unwinding by cooperating ratchet teeth. When the dose is to be injected, a trigger slide is moved to the left causing the ratchet teeth to come out of engagement. This permits the spring to unwind thereby rotating a drive sleeve, drive gear and a drive plunger. The drive plunger is formed with a quick pitch screw thread so that its rotational movement is accompanied by axial movement to cause medicament to be discharged from a cartridge and injected through a needle.

U.S. Pat. No. 5,102,393 describes a autoinjector converted from an intramuscular to a subcutaneous mode of injection comprising a housing having a medicament cartridge assembly mounted within the housing means in a storage position for movement out of the storage position and a releasable stressed spring assembly for moving the medicament cartridge assembly means out of the storage position. The stressed spring assembly is operable in response to a manual actuating procedure which does not require compression of the subcutaneous tissue to effect an intramuscular mode of injection by moving the hypodermic needle of the cartridge assembly outwardly of the housing into the muscle tissue at the injection site of a user and a major portion of the liquid medicament of the cartridge assembly outwardly through the hypodermic needle into the muscle tissue of the user. An injection mode converting structure is secured in a subcutaneous mode position for converting the mode of injection effected by the stressed spring assembly from the intramuscular mode of injection to a subcutaneous mode of injection in which the needle cannot extend substantially beyond subcutaneous tissue at the injection site of the user and a major portion of the liquid medicament enters into the subcutaneous tissue.

U.S. Pat. No. 4,231,368 shows a pistol-like casing for mounting a tubular holder containing a syringe in the gun barrel portion of the casing so it may be cocked in the withdrawn position against the force of a spring and released by movement of an arresting pawl. Pulling back a trigger advances a push rod that first trips the pawl, then brings force to bear against the pistol rod of the syringe. After the needle is driven into the skin by the release of the pawl and the actuating mechanism has been brought to bear against the syringe piston-rod, the injection of the syringe contents can proceed under control of hand feel without any necessity of changing or shifting the hand grip by continuing to pull the trigger back.

U.S. Pat. No. 3,538,916 teaches an injection pistol for intramuscular implantation of encapsulated liquid or solid chemical material into animals. The depth of injection of the needle into the animal muscle is controlled by an injection depth gauge mounted on the injection needle. A shaft means having a slidable plunger means integral therewith is mounted on the frame and is utilized to eject the chemical material from within the injection needle and implant the chemical material into the animal muscle after the needle is thrust into the muscle. The travel of the plunger means within the injection needle is limited by a threadedly adjustable depth stop means mounted on the end of the shaft means opposite to the plunger means.

U.S. Pat. No. 4,270,537 describes a hypodermic syringe and automatic needle insertion device wherein the syringe is biased against a trigger when the needle is in the retracted position. Upon release of the trigger, the syringe and needle are driven forward extending the needle into the underlying tissue. The depth of insertion may be predetermined by the attachment of an interchangeable stop.

Additional examples of the prior art are found in U.S. Pat. No. 4,333,459; U.S. Pat. No. 5,092,376 and U.S. Pat. No. 5,183,465.

SUMMARY OF THE INVENTION

The present invention relates to a diagnostic syringe actuator device for use in combination with a syringe in the removal of tissue, fluid and/or cells for the diagnosis of pathological processes. The syringe includes a hollow syringe body having a syringe plunger at least partially disposed in the proximal end portion thereof and longitudinally movable relative thereto with a probe needle attached to the distal end portion thereof.

The diagnostic syringe actuator device comprises hollow retractor tube having a retractable piston at least partially disposed therein and longitudinally movable relative thereto.

A sabot lock recess and a corresponding sabot lock aperture are formed on the wall of the hollow retractor tube to receive a corresponding sabot lock member to selectively retain a syringe plunger sabot in a first position to maintain the syringe plunger sabot and the syringe plunger attached thereto in an advanced position relative to the hollow syringe body. The sabot lock member comprises an elongated spring element biased outwardly relative to the wall of the hollow retractable tube disposed to engage a sabot lock release and a sabot lock bead or protrusion formed on the inner surface thereof to extend through the sabot lock aperture and engage the syringe plunger to lock the syringe plunger sabot and the syringe plunger in the advanced position.

The sabot lock release comprises a release ring movable between an advanced position and a retracted position on the hollow retractable tube such that when in the advanced position the release ring maintains the elongated spring element in the first or coiled position with the corresponding sabot lock bead or protrusion extending through the corresponding sabot lock groove or recess (sabot/plunger locked configuration) to lock or secure the syringe plunger sabot and the syringe plunger in the advanced position. When the sabot lock release or release ring is moved from the advanced position to a retracted position toward the proximal end portion of the hollow retractor tube, the elongated spring element moves from the first position to the second position to release the syringe plunger sabot and the syringe plunger coupled thereto to move each from the advanced to the retracted position toward the proximal end portion of the hollow retractor tube (sabot/plunger unlocked configuration) when a vacuum has been created in the chamber by moving the retractable piston from the distal end portion of the hollow retractor tube toward the proximal end thereof.

When assembling the diagnostic syringe actuator device and syringe the syringe plunger and the retractor piston are placed in the advanced position relative to the hollow syringe body and the hollow retractor tube respectively with the sabot/plunger lock means in the sabot/plunger locked configuration. The syringe is then attached to the diagnostic syringe actuator device.

Once set up, the probe needle is inserted into the patient. Fluid is drawn by moving the sabot lock release or release ring toward the proximal end portion of the hollow retractor tube releasing the sabot lock member causing the syringe plunder sabot and the syringe plunger to move toward the proximal end of the hollow retractor tube under the negative pressure created by the vacuum within the chamber.

The invention accordingly comprises the features of construction, combination of elements, and arrangement of parts which will be exemplified in the construction hereinafter set forth, and the scope of the invention will be indicated in the claims.

BRIEF DESCRIPTION OF THE DRAWINGS

For a fuller understanding of the nature and object of the invention, reference should be had to the following detailed description taken in connection with the accompanying drawings in which.

Similar reference characters refer to similar parts throughout the several views of the drawings.

DETAILED DESCRIPTION OF THE PREFERRED EMBODIMENT

Figure 1:
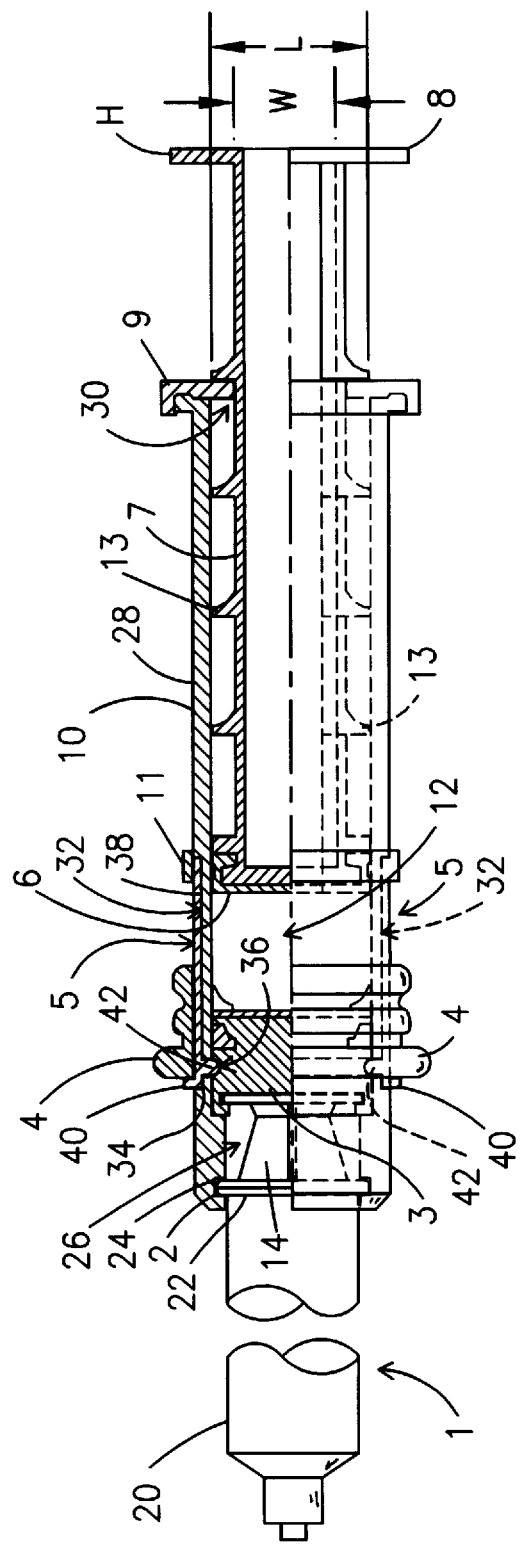
FIG. 1 is a partially cross-sectional side view of the retractable piston syringe adapter of the present invention.
Figure 2:
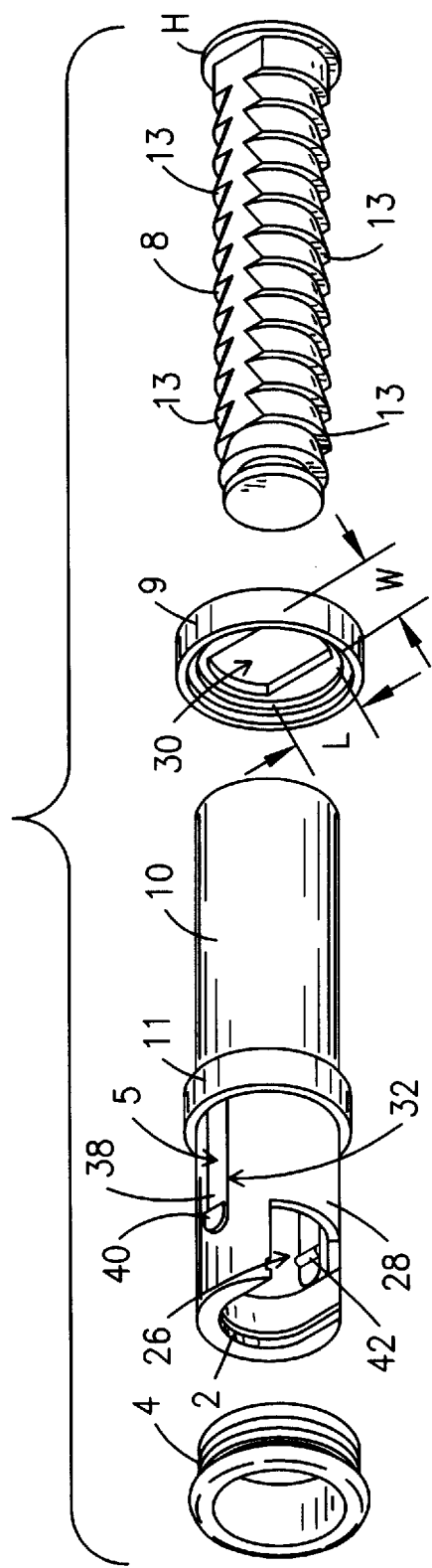
FIG. 2 is a partial exploded perspective view of the retractable piston syringe adapter of the present invention.

As shown in FIGS. 1 and 2, the present invention relates to a retractable piston syringe adapter or diagnostic syringe actuator device for use in combination with a syringe generally indicated as 1 in the removal of tissue, fluid and/or cells for the diagnosis of pathological processes. AS shown in FIG. 1, the syringe 1 includes a hollow syringe body 20 having a plunger or syringe plunger partially shown as 14 at least partially disposed in the proximal end portion thereof and longitudinally movable relative thereto with a probe needle (not shown) attached to the distal end portion thereof. An attachment flange 22 is formed on the proximal end portion of the hollow syringe body 20 to operatively couple the syringe 1 to the diagnostic syringe actuator device as described more fully hereinafter.

The diagnostic syringe actuator device comprises a retractor tube body or hollow retractor tube 10 having a plunger body or retractable piston 8 with a plunger seal or piston seal 6 attached to the distal end portion thereof at least partially disposed therein and longitudinally movable relative thereto.

The hollow retractor tube 10 includes a syringe attachment groove 2 formed on the inner surface 24 at the distal end portion thereof to receive and retain the attachment flange 22 therein to operatively couple the syringe 1 to the diagnostic syringe actuator device. An access slot 26 is formed through the wall 28 of the hollow retractor tube 10 to provide access to the syringe attachment groove 24; while, a power retractor header or end cap 9 including a piston locking aperture 30 with an irregular periphery wherein the length L is greater than the W width to form a first piston lock element is attached to the proximal end portion of the hollow retractable tube. At least one sabot lock recess 32 and a corresponding sabot lock aperture 34 are formed on the wall 28 to operatively receive a corresponding sabot lock member generally indicated as 5 to selectively retain a syringe plunger sabot 3 having a sabot lock groove or recess 36 formed on the periphery thereof in a first position as shown in FIG. 1 to maintain the syringe plunger sabot 3 and the syringe plunger 14 attached thereto in an advanced position relative to the hollow syringe body 20.

The sabot lock member 5 comprises an elongated spring element 38 biased outwardly relative to the wall 28 of the hollow retractable tube 10 secured at the proximal end portion of the corresponding sabot lock recess 32 by a keeper ring/trigger ring stop or retention member 11 disposed to engage a trigger ring or sabot lock release 4 when in the retracted position, a release member limit 40 formed on the outer surface of the distal end portion of the elongated syringe element 38 disposed to engage the sabot lock release 4 when in the advanced position and a sabot lock bead or protrusion 42 formed on the inner surface of the elongated spring element 38 to extend through the sabot lock aperture 34 and engage the sabot lock groove or recess 36 to lock the syringe plunger sabot 3 and the syringe plunger 14 in the advanced position.

The sabot lock release 4 comprises a release ring movable between an advanced position (as shown) and a retracted position on the hollow retractable tube 10 such that when in the advanced position the release ring 4 engages the release limit members 40 and maintains the elongated spring element 38 in the first or coiled position with the corresponding sabot lock bead or protrusion 42 extending through the corresponding sabot lock aperture 34 into operative relationship relative to the sabot lock groove or recess 36 (sabot/plunger locked configuration) to lock or secure the syringe plunger sabot 3 and the syringe plunger 14 in the advanced position (as shown). When the sabot lock release or release ring 4 is moved from the advanced position when at the distal end portion of the hollow retractor tube 10 to a retracted position toward the proximal end portion of the hollow retractor tube 10 and the retention member 11, the elongated spring element 38 moves from the first position to the second position withdrawing the sabot lock bead or protrusion 42 from the corresponding sabot lock groove or recess 36 to release the syringe plunger sabot 3 from the sabot lock member 5 causing the syringe plunger sabot 3 and the syringe plunger 14 coupled thereto to each move from the advanced position (as shown) to the retracted position toward the proximal end portion of the hollow retractor tube 10 (sabot/plunger unlocked configuration) when a vacuum has been created in the chamber 12 by moving the retractable piston 8 from the distal end portion of the hollow retractor tube 10 toward the proximal end thereof.

A plurality of locking tabs or second piston lock elements each indicated as 13 extends outwardly from the exterior of the retractable piston 8 cooperatively forming a second piston lock means. The first and second piston lock means cooperate to selectively lock the retractable piston 8 in one of a plurality of predetermined positions corresponding to the plurality of locking tabs or second piston lock elements 13 longitudinally relative to the hollow retractor tube 10.

A graduated scale 7 may be imprinted or formed on the exterior of the retractable piston 8 to provide a visual indication of the setting or predetermined position of the retractable piston 8 relative to the hollow retractor tube 10 corresponding to a predetermined preset volume of fluid to be extracted or withdrawn from the patient.

The sabot lock member 5, the sabot groove or recess 36 and the sabot lock release 4 cooperatively form a sabot/plunger lock means or mechanism operable in the sabot/plunger locked configuration (as shown) and the sabot/plunger unlocked configuration. The periphery of the piston locking aperture 30 or first piston lock means and the locking tabs 13 or second piston lock means cooperatively form a piston lock means or mechanism operable in the piston locked configuration (as shown) and the piston unlocked configuration.

When assembling the diagnostic syringe actuator device and syringe 1, the syringe plunger 14 and the retractor piston 8 are placed in the advanced position relative to the hollow syringe body 20 and the hollow retractor tube 10 respectively with the sabot/plunger lock means in the sabot/plunger locked configuration. The syringe 1 is attached to the diagnostic syringe actuator device by inserting the proximal end portion of the syringe 1 through the access slot 26 and placing the attachment flange 22 into the attachment groove 2. The retractable piston 8 is then rotated to align the locking tabs or second piston lock elements 13 with the length L of the piston locking aperture 30 or the piston unlocked configuration to permit withdrawal of the retractable piston 8 relative to the hollow retractor tube 10 creating a vacuum in the chamber 12. The volume within the chamber 12 corresponds to the volume of fluid to be withdrawn from the patient into the hollow syringe body 20. The retractable piston 8 is then rotated to align the locking tabs or second piston lock element 13 with the width W of the piston locking aperture 30 or the piston locked configuration to secure or lock the retractable piston 8 in place relative to the hollow retractor tube 10.

Once set up, the probe needle (not shown) is inserted into the patient. Fluid is drawn by moving the sabot lock release or release ring 4 toward the proximal end portion of the hollow retractor tube 10 releasing the sabot lock member 5 causing the syringe plunger sabot 3 and the syringe plunger 14 to move toward the proximal end of the hollow retractor tube 10 under the negative pressure created by the vacuum within the chamber 12.

It will thus be seen that the objects set forth above, among those made apparent from the preceding description are efficiently attained and since certain changes may be made in the above construction without departing from the scope of the invention, it is intended that all matter contained in the above description or shown in the accompanying drawing shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

What is claimed is:

1. A diagnostic syringe actuator device for use with a syringe having a proximal end portion and a distal end portion and including a hollow syringe body with a longitudinally movable syringe plunger at least partially disposed therein with a probe needle attached to the distal end portion of the syringe, in the removal of tissue, fluid or cells for the diagnosis of pathological processes, said diagnostic syringe actuator device comprising:

a hollow retractor tube having a proximal end portion and a distal end portion with a longitudinally movable retractable piston at least partially disposed therein, a longitudinally movable syringe plunger sabot disposed within said hollow retractor tube and attached to the proximal end portion of the syringe plunger, and a sabot lock mechanism selectively movable between a locked position and a unlocked position disposed to engage said syringe plunger sabot when in said locked position to maintain the syringe plunger and said syringe plunger sabot in an advanced position relative to said hollow syringe body, and to disengage said syringe plunger sabot when moved to said unlocked position, such that said syringe plunger sabot and the syringe plunger move from said advanced position toward the proximal end of said hollow retractor tube when said retractable piston has been at least partially retracted toward the proximal end of said hollow retractor tube to create a vacuum within the hollow syringe body whereby material is extracted from a patient through the probe needle and into the hollow syringe body.

2. The disgonstic syringe actuator device of claim 1 wherein said syringe plunger sabot includes an outer periphery with a sabot lock groove to receive said sabot lock protrusion.

3. The diagnostic syringe actuator device of claim 2 wherein said sabot lock member, said sabot groove and said sabot lock release cooperatively form said sabot/plunger lock mechanism operable in said sabot/plunger locked configuration and said sabot/plunger unlocked configuration.

4. The diagnostic syringe actuator device of claim 3 further including an end cap piston locking aperture with an irregular periphery wherein the length is greater than the width to form a first piston lock attached to the proximal end portion of said hollow retractor tube and a plurality of locking tabs to form a second piston lock extends outwardly from the exterior of said retractable piston cooperatively forming a piston lock means; said piston lock means locks said retractable piston in one of a plurality of predetermined positions corresponding to said plurality of locking tabs longitudinally relative to said hollow retractor tube.

5. The diagnostic syringe actuator device of claim 4 wherein said or first piston lock and said second piston lock cooperatively form a piston lock mechanism operable in said piston lock configuration and said piston unlocked configuration.

6. The diagnostic syringe actuator device of claim 1 wherein the sabot lock member comprises an elongated spring element having an inner surface biased outwardly relative to said hollow retractor tube.

7. The diagnostic syringe actuator device of claim 6 wherein a sabot lock protrusion is formed on the inner surface of said elongated spring element to extend through a sabot lock aperture found in said hollow retractable tube to engage and lock said syringe plunger sabot in said advanced position.

8. The diagnostic syringe actuator device of claim 7 further including a sabot lock release movable between a locked position and an unlocked position mounted on said hollow retractable tube such that when in said locked position said sabot lock release engages said elongated spring element in said first position with said sabot lock protrusion extending through said corresponding sabot lock aperture into operative relationship relative to said sabot lock groove to lock said syringe plunger sabot and the syringe plunger together and when said sabot lock release is moved from said locked position to said unlocked position said elongated spring element moves from the said first position to the said second position withdrawing said sabot lock protrusion from said corresponding sabot lock groove to release said syringe plunger sabot causing said syringe plunger sabot and the syringe plunger to move toward said proximal end portion of said hollow retractor tube.

9. The diagnostic syringe actuator device of claim 8 wherein said sabot lock release comprises a release ring slidably movable between an advanced position and a retracted position on said hollow retractable tube.

10. The diagnostic syringe actuator device of claim 9 wherein a release member limit is formed on said elongated syringe element to engage said release ring when in said advanced position.

11. The diagnostic syringe actuator device of claim 1 wherein said hollow retractor tube includes a syringe attachment groove formed on the inner surface at the distal end portion thereof to receive and retain an attachment flange formed on the hollow syringe body therein to operatively couple the syringe to said diagnostic syringe actuator device.

12. The diagnostic syringe actuator device of claim 11 further including an access slot formed through said wall of said hollow retractor tube to provide access to said syringe attachment groove.

* * * * *